(12) United States Patent
Huang et al.

(10) Patent No.: US 7,715,011 B2
(45) Date of Patent: May 11, 2010

(54) METHODS FOR USING LIGHT REFLECTION PATTERNS TO DETERMINE LOCATION OF PITH AND CURVATURE OF THE ANNUAL RING

(75) Inventors: Chih-Lin Huang, Bellevue, WA (US);
Stanley L Floyd, Enumclaw, WA (US);
Mark A Stanish, Seattle, WA (US);
David N Bogue, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 811 days.

(21) Appl. No.: 11/536,940

(22) Filed: Sep. 29, 2006

(65) Prior Publication Data

US 2008/0078473 A1 Apr. 3, 2008

(51) Int. Cl.
*G01N 21/55* (2006.01)
(52) U.S. Cl. .................................... 356/445
(58) Field of Classification Search ... 356/237.1–237.5, 356/445–448
See application file for complete search history.

(56) References Cited

U.S. PATENT DOCUMENTS

| 4,606,645 | A | * | 8/1986 | Matthews et al. ............ 356/446 |
| 4,831,545 | A | | 5/1989 | Floyd |
| 4,916,629 | A | * | 4/1990 | Bogue et al. .................. 702/40 |
| 4,926,350 | A | | 5/1990 | Bechtel |
| 5,252,836 | A | | 10/1993 | Matthews |
| 6,293,152 | B1 | | 9/2001 | Stanish |
| 6,305,224 | B1 | | 10/2001 | Stanish |
| 2008/0074670 | A1 | | 3/2008 | Carman |
| 2008/0078473 | A1 | | 4/2008 | Huang |

\* cited by examiner

*Primary Examiner*—Michael P Stafira
(74) *Attorney, Agent, or Firm*—Rachael Vaughn

(57) ABSTRACT

Methods are provided for using light reflection patterns to determine various properties of fibrous materials, such as wood. More specifically, the present invention relates to methods for determining a dive angle for grain. Further, the present invention relates to methods for using information in T2 plots, combined with knowledge of the microstructure of a wood sample surface, to find pith location and/or ring curvature.

16 Claims, 23 Drawing Sheets

Surface Angle = 0°
Dive Angle = 0°

Surface Angle = 30°
Dive Angle = 0° p1: projected pith location on side one
M11: the first location of maximum peak difference on side one
M21: the second location of maximum peak difference on side one p2: projected pith location on side two
M12: the first location of maximum peak difference on side two
M22: the second location of maximum peak difference on side two

METHODS FOR USING LIGHT REFLECTION PATTERNS TO DETERMINE LOCATION OF PITH AND CURVATURE OF THE ANNUAL RING

FIELD OF THE INVENTION

This invention relates generally to methods for using light reflection patterns to determine various properties of fibrous materials, such as wood.

BACKGROUND OF THE INVENTION

Spiral grain, taper, butt swell, knots, growth damage, and cutting patterns are factors related to grain deviation from the longitudinal edge of a piece of lumber. Grain deviation includes surface angle and dive angle. Surface angle is the angle between the grain direction (direction of tracheid axis) and the longitudinal edge on the viewing surface of the piece of lumber. Dive angle is the tilting angle of the tracheid axis with respect to the surface plane. Because wood is a highly anisotropic material, the grain direction of wood has a significant effect on strength, stiffness, and dimensional stability of wood products. The grain direction measurement is very useful for twist prediction, lumber strength grading, and knot delineation. Different scanning technologies that measure grain direction primarily identify lumber defects, evaluate lumber strength, and predict lumber warp propensity. Several of these technologies rely on a phenomenon known as the "tracheid-effect" whereby patterns of light scatter (both specular and diffuse) can be interpreted to infer geometric properties of the small fibers that constitute materials such as wood. A tracheid effect (Referred to as the T1 effect) is described in U.S. Pat. No. 3,976,384. The reflected shape of a round spot of laser light will appear elongated when reflected off the surface of wood. The direction of this elongation follows the axis of the tracheids. Another example, the "T2" concept described in U.S. Pat. No. 4,606,645 involves the projection of collimated light onto a fibrous web. The direction of the strongest reflection is perpendicular to the fiber axes. For diving grains, light reflected from the side and bottom walls of open tracheids cause the locations of the highest local reflection intensity to move toward the diving direction. The reflected light on end grain or knot is scattered or diffused. These phenomena are demonstrated in FIG. 1.

A laser scanning instrument made by Plessey Company (UK) includes a ring of 72 sensors with 5° (degree) spacing and measures the 45° (degree) light reflection from a laser shining straight down onto a wood surface. This is shown in FIG. 2. An ideal plot of the reflected light intensities versus the azimuth angle around the ring has two symmetric peaks (local maximum intensities) and two valleys (local minimum intensities). Surface angle is indicated by the shift in peak locations (shown in FIG. 3). Diving or tilting brings the peaks closer together if the grain dives in the same direction, or farther apart if the grain dives in the opposite direction (see FIG. 4).

The surface and dive angles can be calculated using the azimuth angle locations of these two peaks and the angle of the reflected light from the wood surface, otherwise referred to as the view angle (Matthews 1987). The applicable formulas are provided below:

$$\text{Surface angle} = (\text{peak1} + \text{peak2})/2 - 180$$

$$\text{Dive angle} = \arctan(\tan(\text{view angle}/2) \cdot \cos((\text{peak1} - \text{peak2})/2))$$

These formulas were developed based on the assumption that the distribution of the orientation of the side wall on the surface is uniform. This assumption is valid only when the grain pattern has either perfectly vertical or perfectly flat grain and results in symmetric peaks of the same height. According to the formulas, where the view angle is known, the only data needed to calculate the surface and dive angles are the positions of these two peaks. A difference in peak heights can indicate the existence of ring curvature on the wood surface, which deviates from the assumption. There are errors involved in T2 dive angle calculation when peaks are too close together, or when one peak is significantly higher than the other, or when both situations occur. These errors can be observed by measuring the same spot while tilting or rotating the sample (Schajer & Reyes 1986, Prieve 1985).

Reducing the number of sensors and improving peak finding algorithms have been frequent research subjects of the T2 technology. A simplified design using 10 sensors demonstrated that sensors can be placed at a few critical locations to achieve a sufficient accuracy with a mean error in a range from 0.5 degree to 1.8 degree (Schajer 1986). It was found that to achieve these accuracies, the ring of sensors needed to have uniform sensitivity. The use of inverse parabola interpolation schemes also greatly reduced the errors of peak finding. The observed systematic errors were also found to be larger in dive angle calculation than in the surface angle calculation (Schajer & Reyes 1986). Variations of the twin-peak intensity pattern were observed to be related to surface roughness, damages, wane, and/or sample tilting. (Prieve 1985).

Most tracheid-effect interpretation models assume that the tracheid has a circular cross-section (FIG. 11 in U.S. Pat. No. 4,606,645) and no variation in the orientation of the side walls of the opened tracheid (referred to as the "simple model of a wood surface" (Matthews 1987)).

Surface roughness, ring curvature, and dynamic measuring condition (measuring while the sample is moving) are a few of the factors that affect the consistency of the surface and dive angle measurements, especially for high dive angles. The systematic "errors" reported in previous work (Schajer & Reyes 1986) (illustrated in FIG. 5) may be effects of certain unique patterns of wood structure, and therefore may convey useful information about the structure.

Such inconsistency in measuring dive angles around a knot tends to cause over-estimation of the size of a knot. Accurate estimation of the size of knots optimizes the recovery of clear wood from remanufacturing operations and improves the accuracy of sorting visual grades of structural lumber. The location of pith is required to estimate the size of knots within a piece of lumber. If we can measure the ring curvature or the pith location using a T2 scanning system, we can improve the accuracy of knot size estimation.

Lumber twist propensity can be inferred from the dive and surface angle patterns within the clearwood (no knots) areas of the lumber. Accordingly, a need exists for a method of using T2-related information to infer clearwood locations and exclude data from non-clearwood locations. A further need exists for a method of using other information in T2 reflection patterns, combined with the knowledge of the wood surface microstructure, to find pith location and ring curvature.

BRIEF DESCRIPTION OF THE DRAWINGS

The embodiments of the present invention are described in detail below with reference to the following drawings.

DETAILED DESCRIPTION OF THE INVENTION

The present invention relates generally to methods for using light reflection patterns to determine various properties of fibrous materials, such as wood. Wood samples may be any type, including green, dried, or any other form or condition of lumber known to those skilled in the art. More specifically, the present invention relates to methods for determining a dive angle for grain. Further, the present invention relates to methods for using information in light reflection patterns, combined with knowledge of the microstructure of a wood sample surface, to find pith location and/or ring curvature. The light that is projected toward the fibrous material may be any type of light capable of producing a T2 effect. Such types of light are known by those skilled in the art.

The invention may be better understood by the following example:

Example 1

Figure 6:
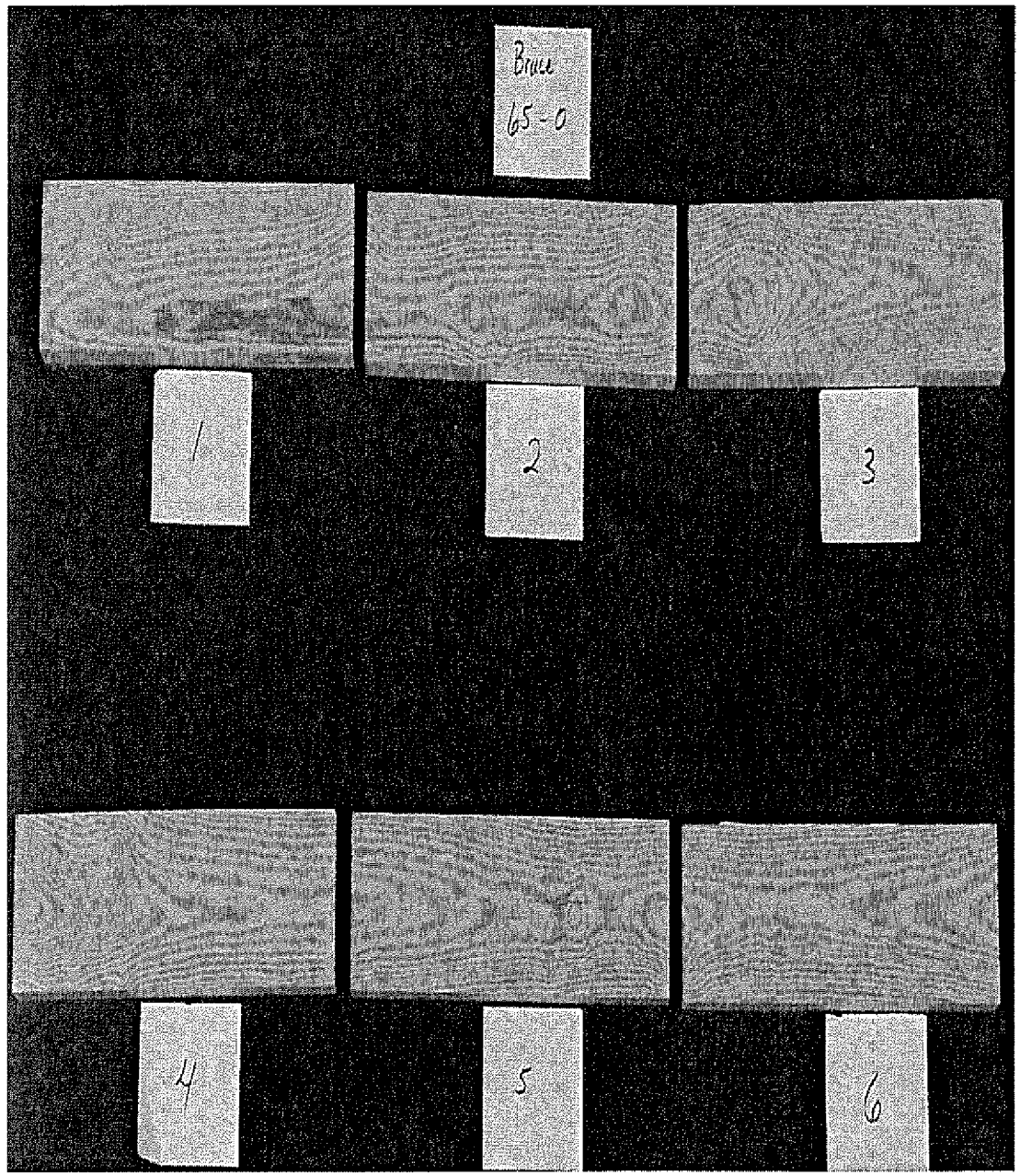
FIG. 6 is an example of sixteen-inch segments taken from 8 foot long, 2 inch by 4 inch boards.

A batch of wood samples included 23 pieces of eight-foot 2×4 (2 inch by 4 inch) pieces, each cut at different locations from one of 23 pieces of 16 foot lumber from Weyerhaeuser Company owned and operated mills (Dierks and Bruce). Warp of the lumber was quantified after conditioning at different relative humidities. Each piece of the 2×4 batch was cut into 16 inch segments. Examples of the wood pieces are provided in FIG. 6.

Figure 7:
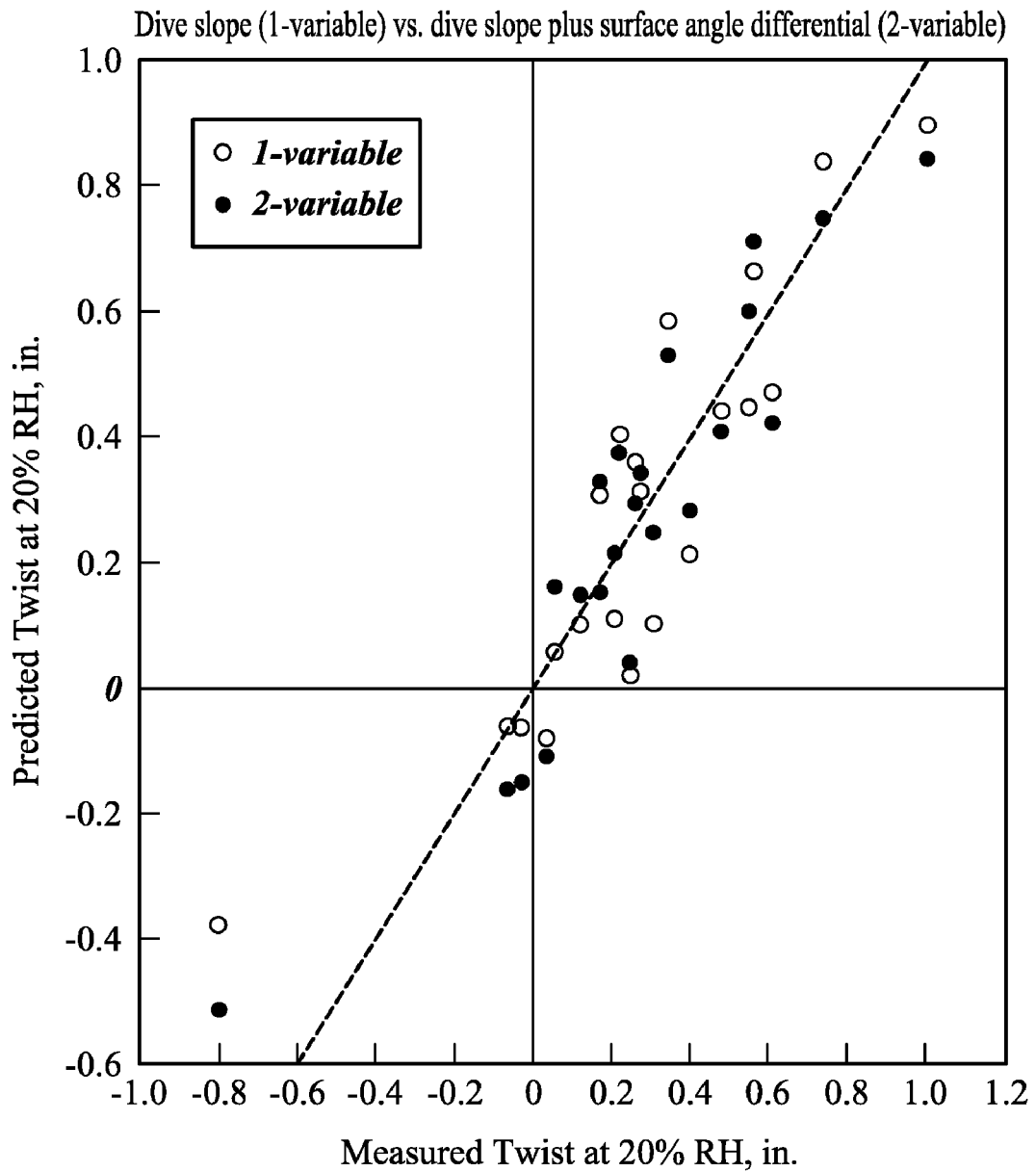
FIG. 7 is a plot of the results of twist prediction using dive angle calculated from the T2 Scanning System.

Fifteen T2 reflection measurements were taken on both wide faces of each piece in a 5-wide×3-along grid pattern. (total of 30 points per piece). Surface and dive angles were determined from these measurements. This dataset was used as the input for a twist model based on a method described in U.S. Pat. No. 6,293,152. Some of the high dive angle outliers were excluded or masked from the twist prediction model. The results were quite good and are illustrated in FIG. 7.

Figure 8:
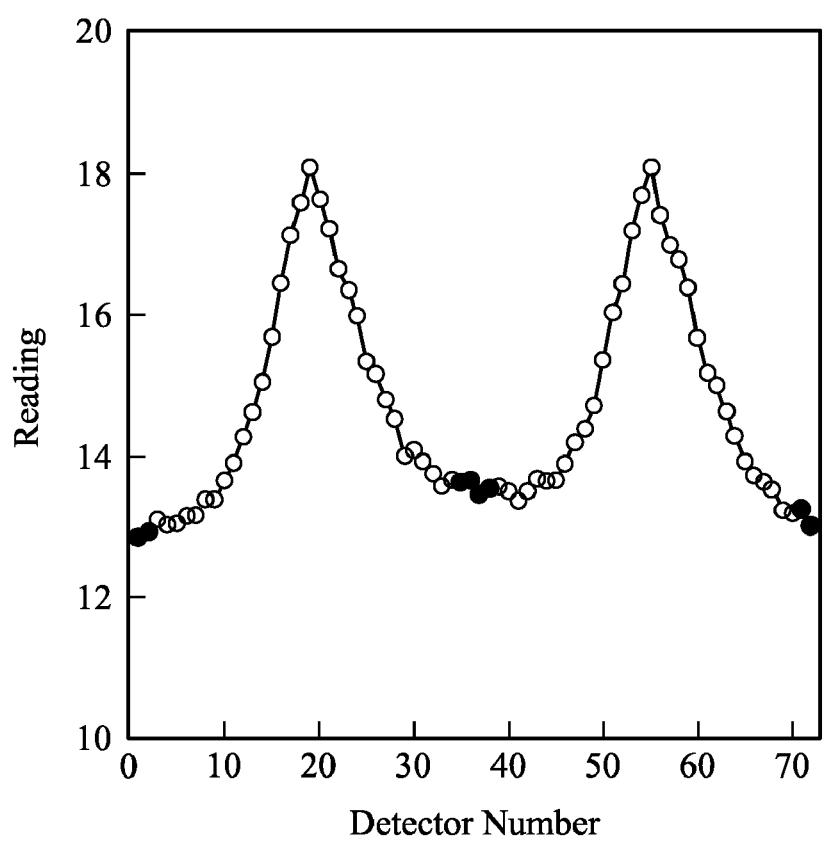
FIG. 8 is a plot of data from the four closest sensors at the bottom of the valleys V1 and V2.

Using the previously described Plessey T2 sensor composed of a ring of 72 detectors, we observe local minimum intensities (valleys) at detector locations that are aligned with the tracheid axis of the illuminated wood surface. Referring to FIG. 8, it is expected that the first valley to occur in the vicinity of sensor locations 71, 72, 1 and 2 and the second valley to occur in the vicinity of sensor locations 35, 36, 37 and 38. Valley intensities are defined as follows:

V1=average intensity of detectors 71, 72, 1, and 2.
V2=average intensity of detectors 35, 36, 37 and 38.

For a wood surface with no dive or surface angle, the local maximum intensities (peaks) are perpendicular to the tracheid axis. The first peak is in the vicinity of sensor locations 17, 18, 19, and 20 and the second peak in the vicinity of sensor locations 53, 54, 55, and 56. Peak intensities are defined as follows:

P1=average intensity of detectors 17, 18, 19, and 20.
P2=average intensity of detectors 53, 54, 55, and 56.

Figure 9:
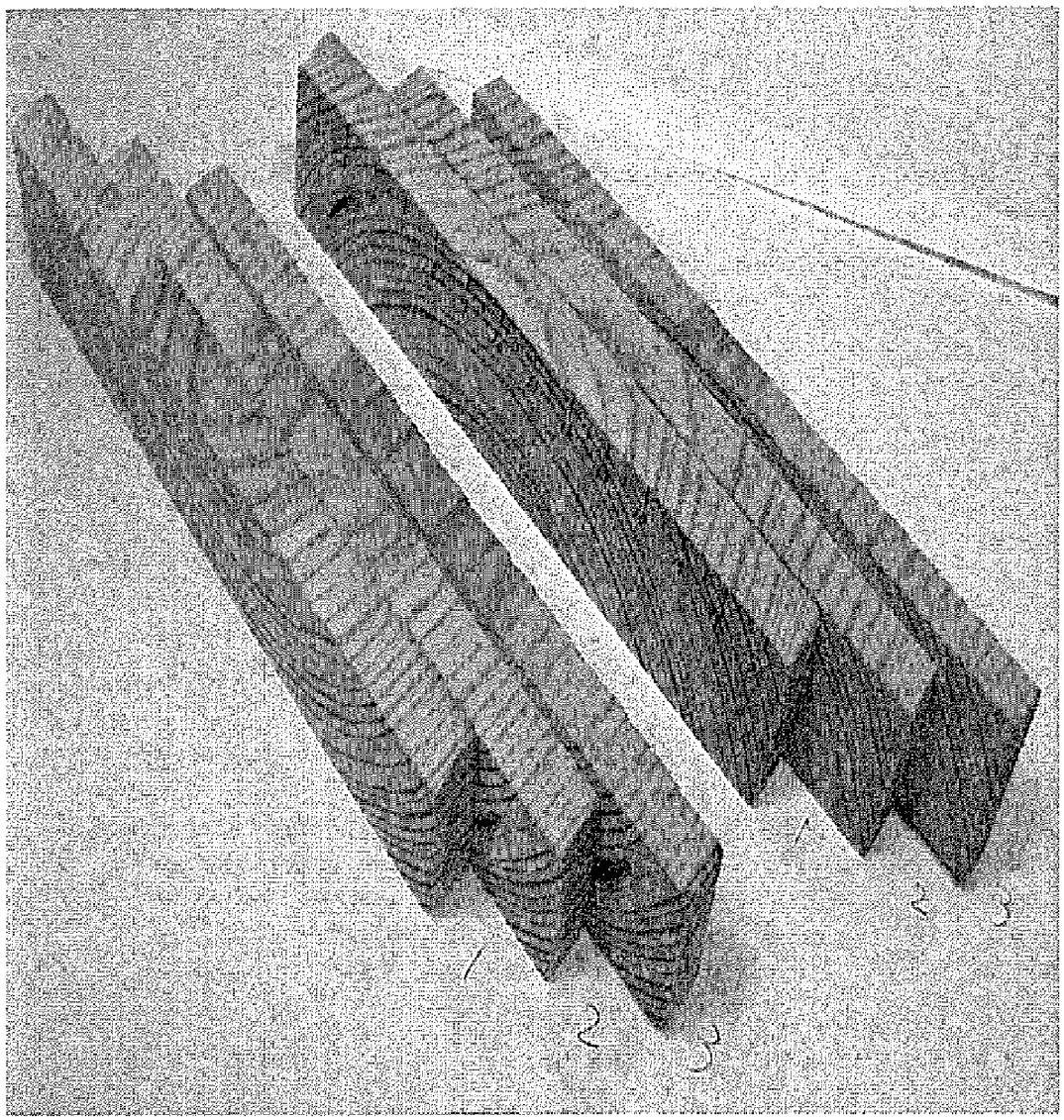
FIG. 9 is an example of wood strips with ~0°, ~7.5°, and ~15° dive angles on top (Sample A) and bottom (Sample B) surfaces of a lumber segment (samples A and B Groups, the major ticks are ½" Spacing)

A relationship between the ring curvature and peak height differences (P1–P2) was observed in the results of the batch of 16" samples. A second batch of samples with known dive angle and ring curvature was prepared for further investigation of the observed relationship. Five segments of lumber, each with different ring width and ring curvature, were selected and six half-inch wide strips of specimens were cut from each lumber segment. Three top surfaces and three bottom surfaces of the strips were planed to produce ~0°, ~7.5, and ~15° dive angles. These samples are shown in FIG. 9. T2 scans were taken on the planed surface of the strips using quarter-inch spacing.

1. Using Peak Finding and Valley Differences to Predict Dive Angle

Figure 10:
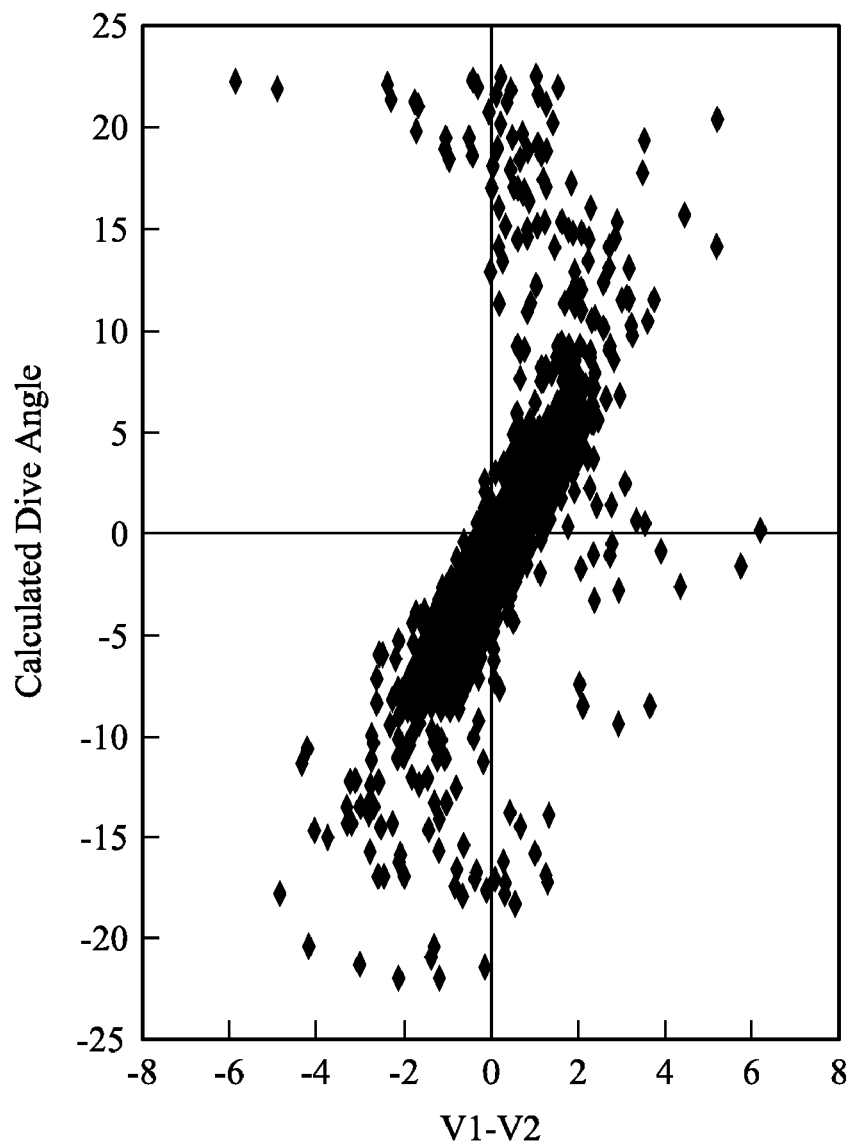
FIG. 10 is a plot showing the relationship between V1–V2 and the calculated dive angle.

The correlation between V1–V2 dive angle is better at low (<10°) dive angles (see FIG. 10). Accordingly, the predicting model should be built using data in this range. The reflected intensity patterns must be normalized to minimize noise effects caused by a variety of factors such as surface roughness, detector sensitivity variation, etc.

Within a T2 detector ring, those that are oriented at azimuth angles in alignment with the tracheid axis will detect the lowest amount of specular reflection (relative valleys). These relative valleys are much "flatter" tan the peaks (i.e. similar low intensity levels are sustained among adjacent detectors). As a result, the difference between intensities of the two relative valleys can be observed by multiple detector pairs in those flat regions. As a result, if surface angle is small (<10 degrees) the relative valley differences will be detected by sensor pairs that are aligned with the axis of the lumber (and not necessarily the axis of the tracheids). Thus measuring the difference between relative valley intensities can be accomplished with as few as 2 detectors positioned 180 azimuth degrees from each other and oriented along the length axis of the lumber.

Figure 1:
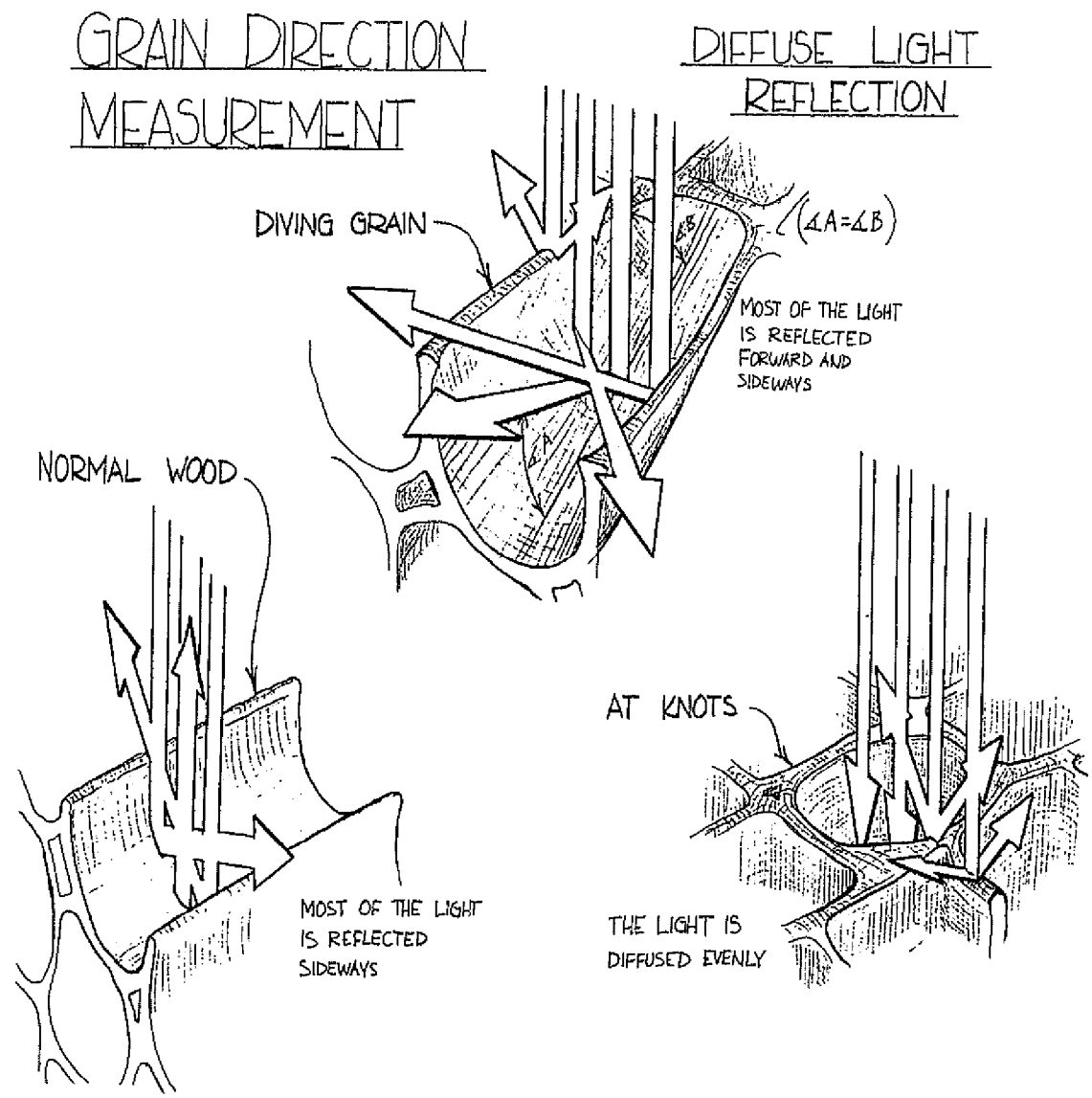
FIG. 1 is a diagram of the reflections of light on a wood surface having flat, dive and vertical grains.
Figure 2:
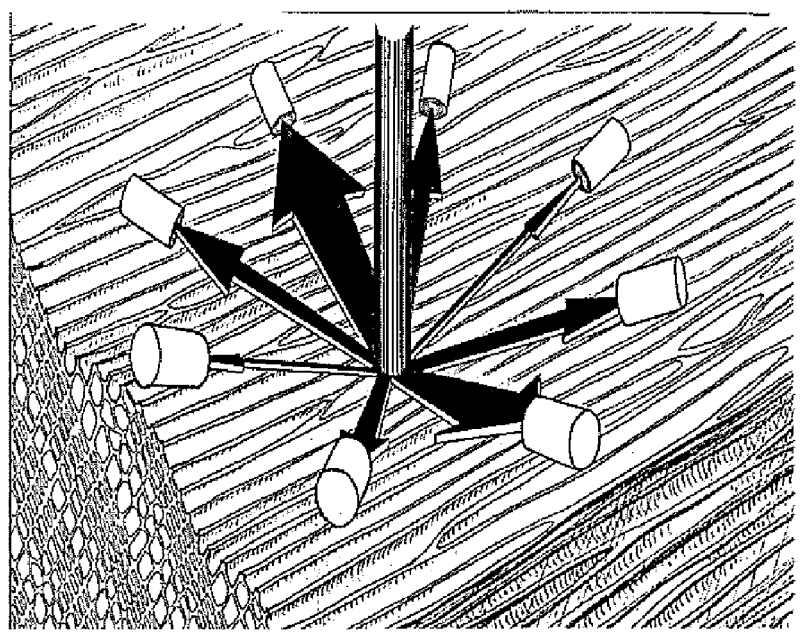
FIG. 2 is a T2 scanning system.
Figure 2:
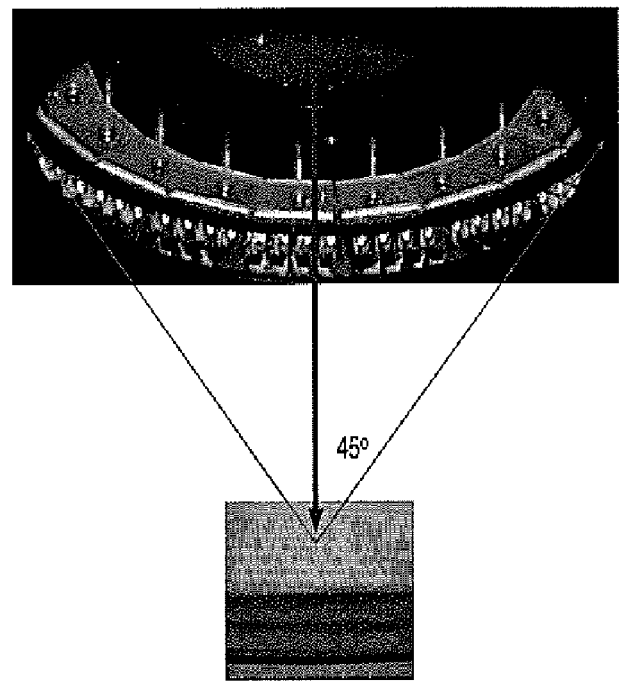
Figure 3:
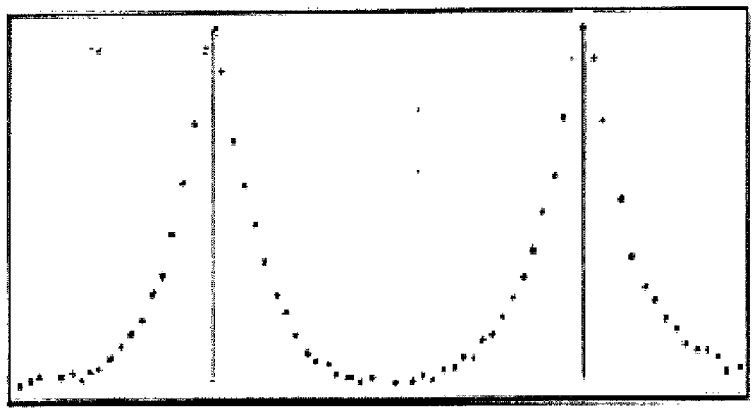
FIG. 3 is a plot of intensity traces of 72 sensors showing the shift in peak locations in the bottom plot due to a 30° surface angle.
Figure 3:
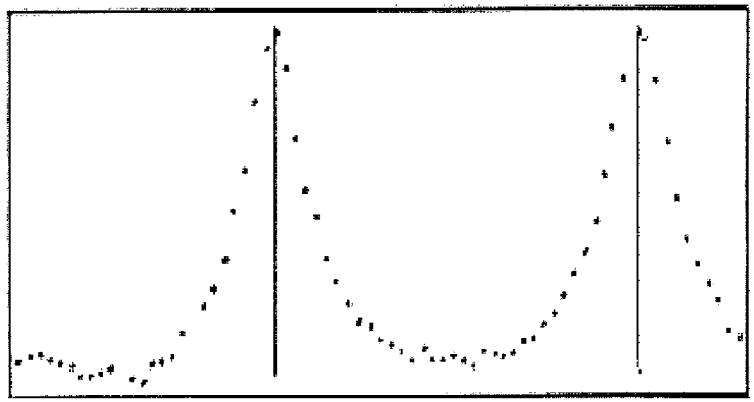
Figure 4:
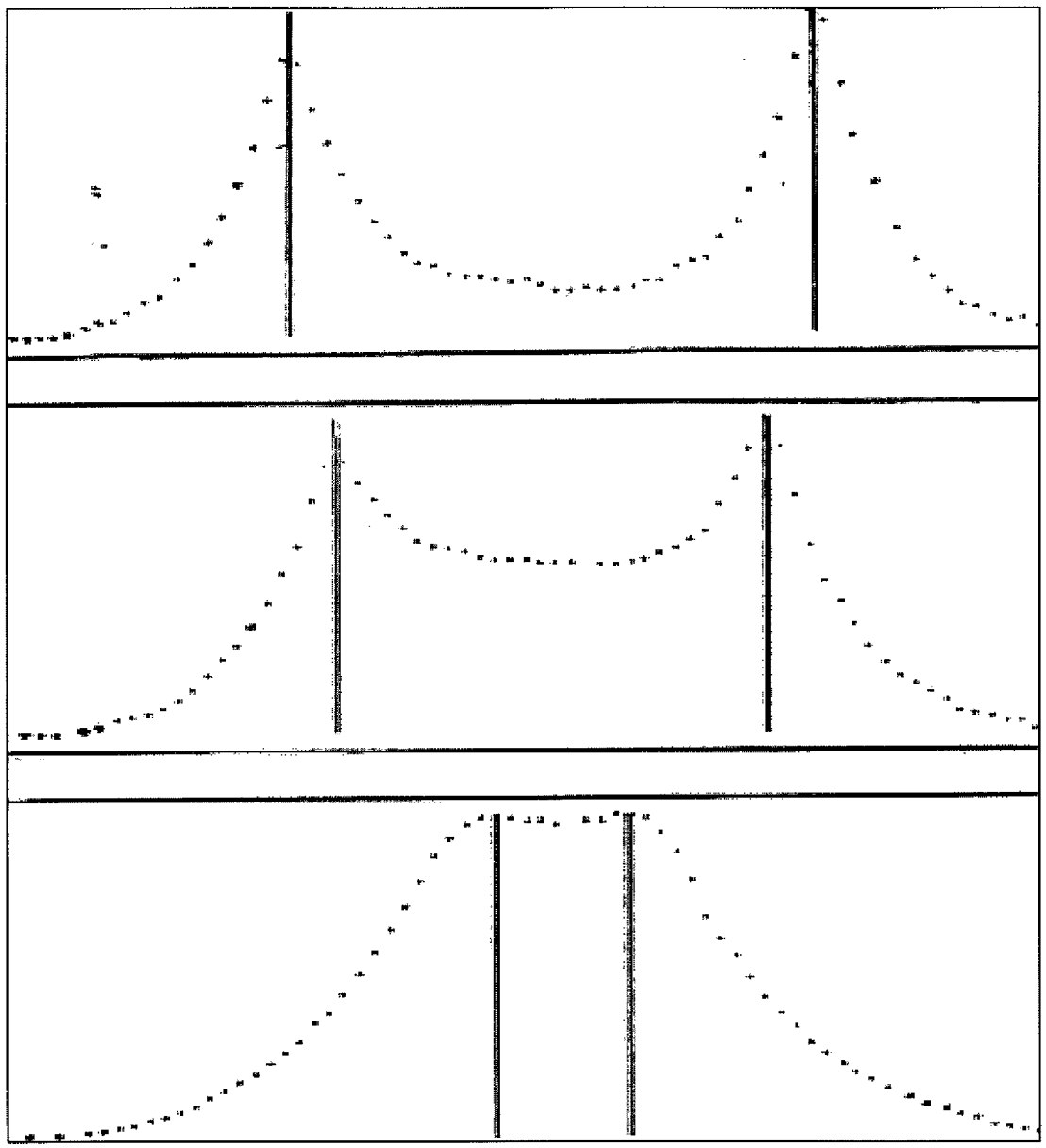
FIG. 4 is a plot of intensity traces of increasing dive angle from top to bottom (surface angle=0° dive angle from top to bottom: 0°, 9°, and 13°); note that the peaks are closer together as the dive angle increases and that the differences between the intensities at the valleys (the reflection from the bottom wall) increases with the dive angle.
Figure 5:
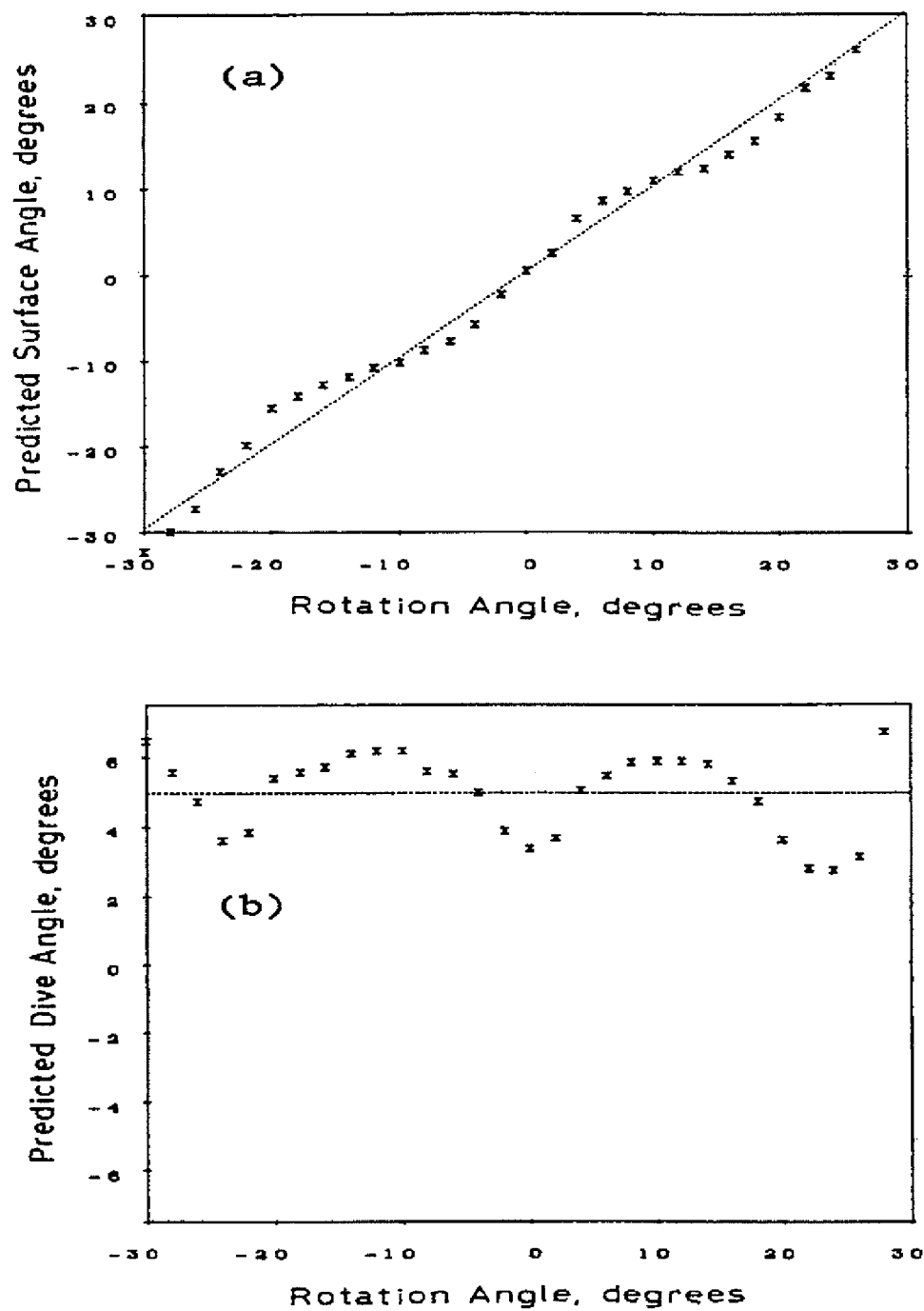
FIG. 5 illustrates a plot of predicted surface angle vs. specimen rotation angle and a plot of predicted dive angle vs. specimen rotation angle (note the greater systematic errors in dive angle than in surface angle prediction)
Figure 11:
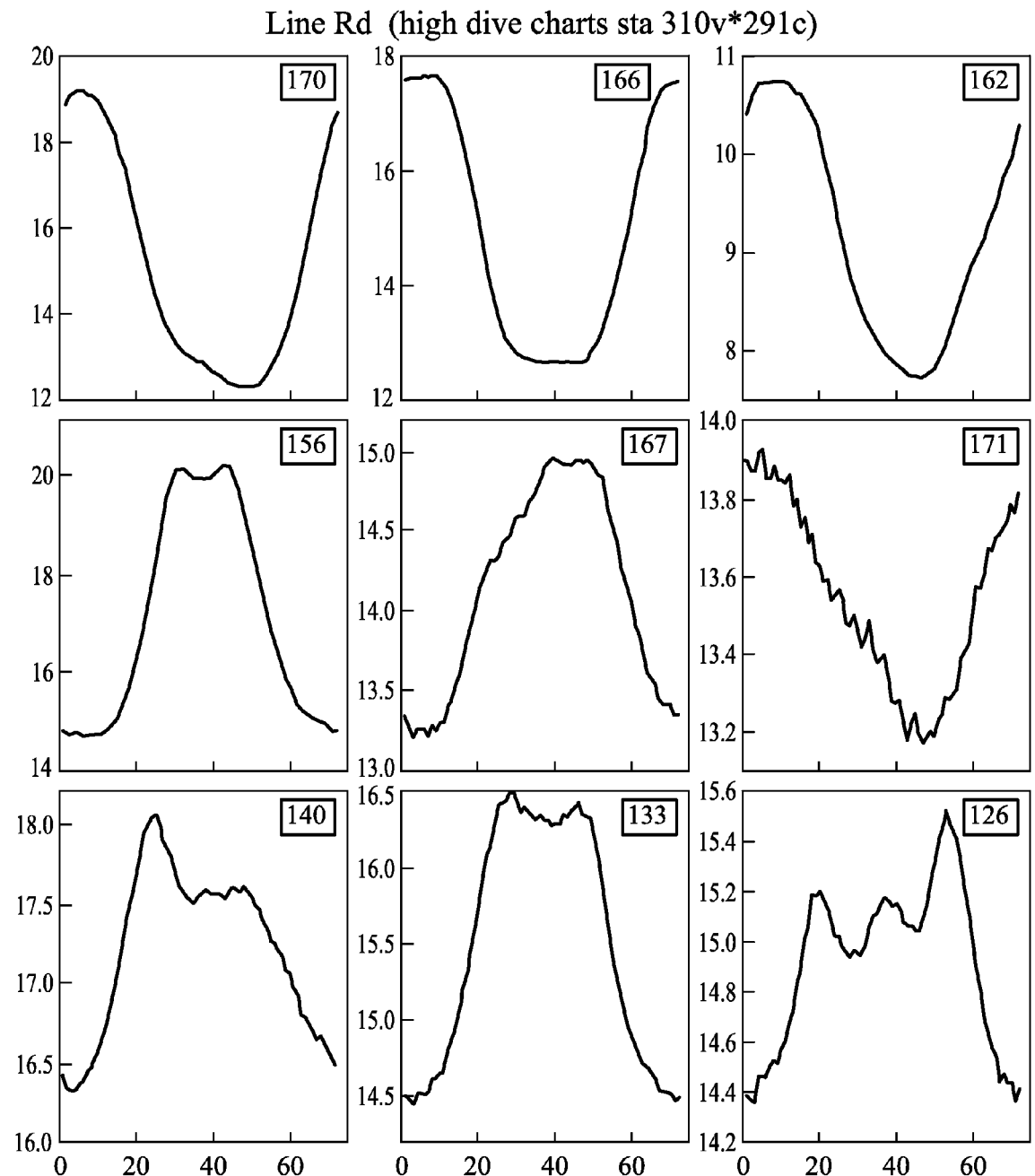
FIG. 11 provides examples of intensity plots of high dive angle areas in a wood sample.

For smaller dive angles, the peaks of the intensity patterns are well-separated and easy to see (FIG. 3) and the peaks can be consistently identified by peak finding algorithms. These algorithms are known by those skilled in the art. When the dive angle is large, the two peaks merge together and are more difficult to separate because the intensity patterns merge into a single broad peak with single or multiple humps and a broad valley (see FIG. 11). Consequently, it is very difficult to find the location of the two peaks when the dive angle is large. If the surface angle is small, a large dive angle can be predicted via the formula V1–V2 using the established dive angle calibration model. It is likely that predicting dive angle using the valley difference yields more consistent results than using the peaks, especially when the dive angle is large.

Figure 12:
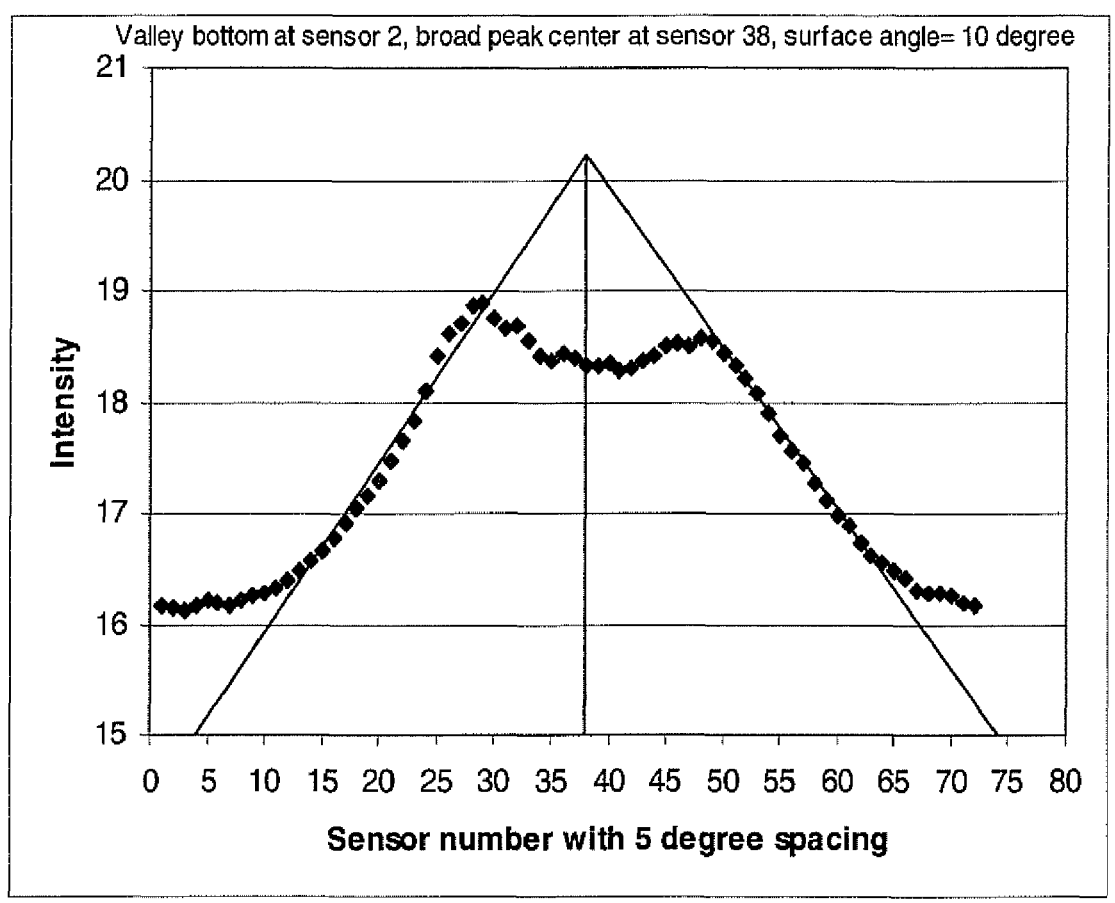
FIG. 12 is plot of an example of a determined surface angle on a curve showing only one single broad peak (a typical T2 sensor intensity trace at a high dive angle area)

Dive angle estimation is more complicated when surface and dive angles are both large, as when the 180 degree between-valley spacing is maintained but the positions of the sensors are rotated. The true locations of V1 and V2 can be determined by finding either the center of the broad valley or the broad peak. Different algorithms, such as the one used to analyze the X-ray diffraction patterns of softwood tracheid (Verrill et al. 2001), can be used to find the locations of the valleys and the peaks. Visually, we can find the bottom of the valley and the center of the broad peak by the intersection of two lines drawn tangent to the peak (as illustrated in FIG. 12).

Once we know the true locations of V1 and V2, we can calculate V1–V2 to predict dive angle using the model. Referring to the plot of intensity vs detector azimuth angle, surface grain angle can be estimated from the intersection of lines tangent to the flanks of the peaks. Other methods such as described in U.S. Pat. No. 3,976,384 can also be used to measure surface angle. Such methods are known by those skilled in the art.

The reliable methods for predicting dive angle under different dive and surface angle conditions are summarized in Table 1.

TABLE 1

Recommended Method for Predicting Dive Angle under Different Surface and Dive Angle Conditions

|  | Low Dive Angle | High Dive Angle |
| --- | --- | --- |
| Low Surface Angle | V1–V2 Peak finding | V1–V2 |
| High Surface Angle | T1 then V1–V2 Peak finding | T1 then V1–V2 |

Figure 13:
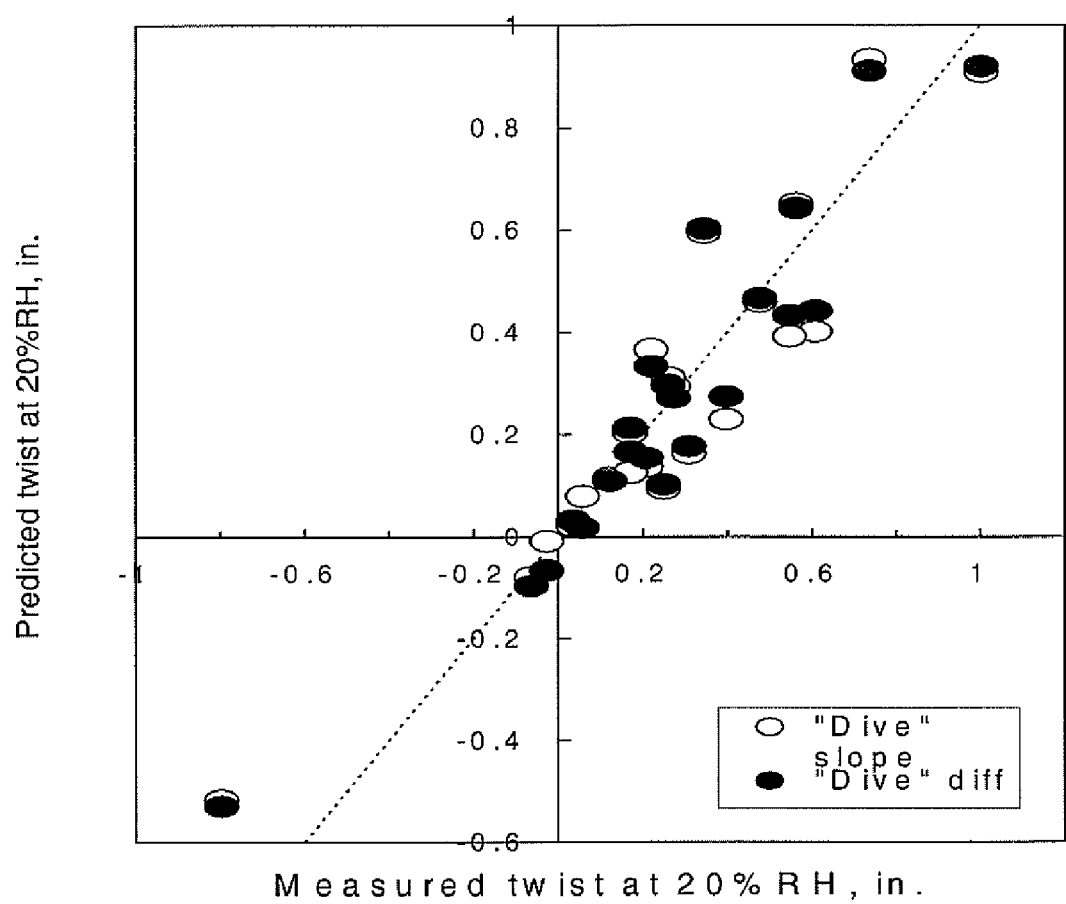
FIG. 13 is a plot of the results of twist predictions using V1–V2 calculated from the T2 scanning system (The open and filled symbols are the results using the slope and differences of dive angles across the board respectively and both results are similar to that in FIG. 7)

As we see in FIG. 13, using the formula V1–V2 to calculate dive angles as the input to the twist model produced similar prediction of lumber twist. Based on these results, we can simply use two single sensors, or two groups of sensors placed at the 0° and 180° positions, along the lumber axis to estimate dive angles for twist prediction. To further improve accuracy, we can estimate surface grain angle from the diffuse (T1) "tracheid effect" pattern generated by the same laser used for the T2 measurement.

Figure 14:
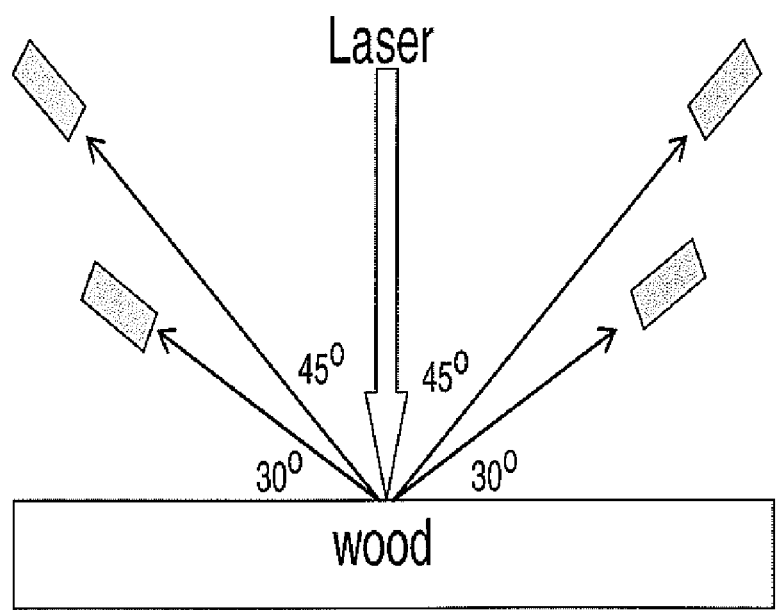
FIG. 14 is a diagram of positioning sensor pairs at more than one detection angle to derive a gradient of dive angle around a knot.

If only one pair of sensors with 45° view angle is used, the maximum dive angle prediction is half the view angle (22.5°). As the dive angle increases beyond the half angle, the reflection intensity at the valley decreases. Multiple pair of sensors can be positioned at different view angles (as shown in FIG. 14) to extend the range and improve the accuracy dive angle measurement.

2. Peak Height Differences and Ring Curvature

Its varied knot structure makes grading SYP (Southern Yellow Pine) lumber a challenge. Pith-containing and non-pith-containing lumber are well known to have contrasting wood properties. The ability to identify the location of pith will further improve knot volume assessment and strength grading of SYP and other species. Ring curvature or the radius to pith also helps twist prediction, which is important for warp grading.

The approximate location of pith relative to the surface of lumber can be derived by comparing knot count, knot size and the grain swirling pattern around a knot between the sides and between the edges of a piece of lumber (U.S. Pat. No. 4,916,629). Such method is applicable only when there are knots on opposite sides of the lumber. A more useful method would allow us to obtain similar information using the clearwood area, which normally occupies most areas on lumber surfaces.

Figure 15:
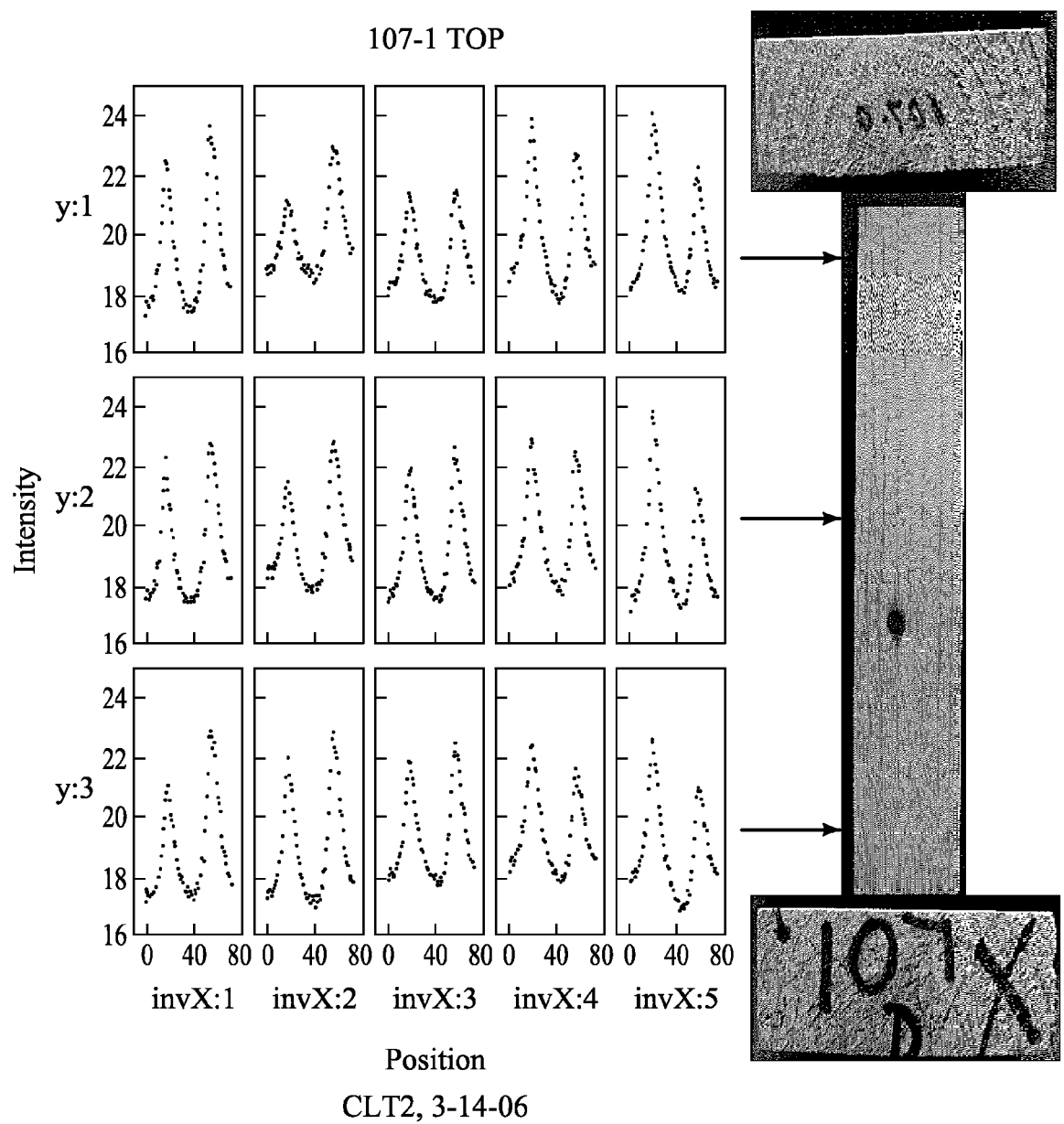
FIG. 15 is a plot of reflected light intensity traces of 15 Areas on a 16 inch long segment of a 2 inch by 4 inch board (note that variation of peak heights tend to follow the ring curvature)

An interesting observation on the 16" sample is the systematic pattern between the peak height difference and the ring curvature (see FIG. 15). The results suggest that information from peak differences can be used to predict ring curvature.

Figure 16:
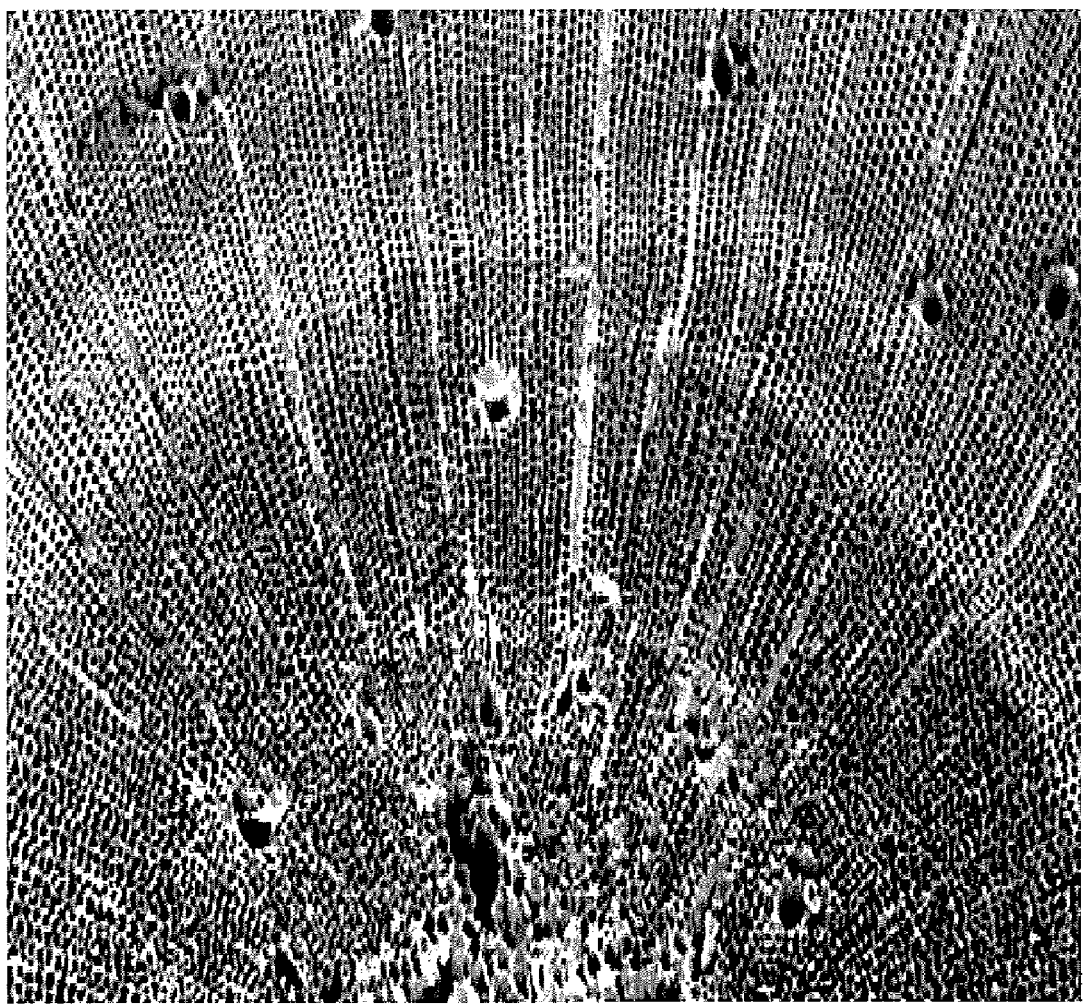
FIG. 16 is a SEM photograph of the cross-section of loblolly pine seedling showing the alignment of tracheids in a radial direction.
Figure 17:
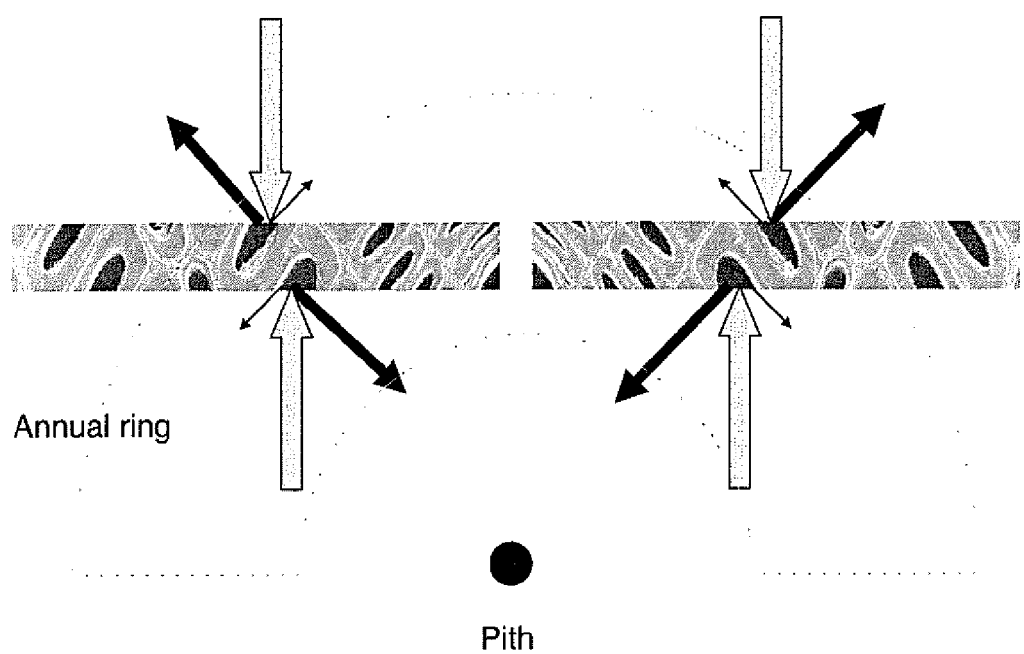
FIG. 17 is a diagram showing the asymmetric reflection patterns due to an exposed lumen that is lop-sided.

The direction of the tangential wall exposed on a lumber surface fluctuates according to the angle of the file of tracheids relative to lumber surface (FIG. 16). The exposed lumen on the lumber surface may have asymmetric side walls and different angles of bottom wall which reflect different amounts of light to the sensors (see FIG. 17).

Figure 18:
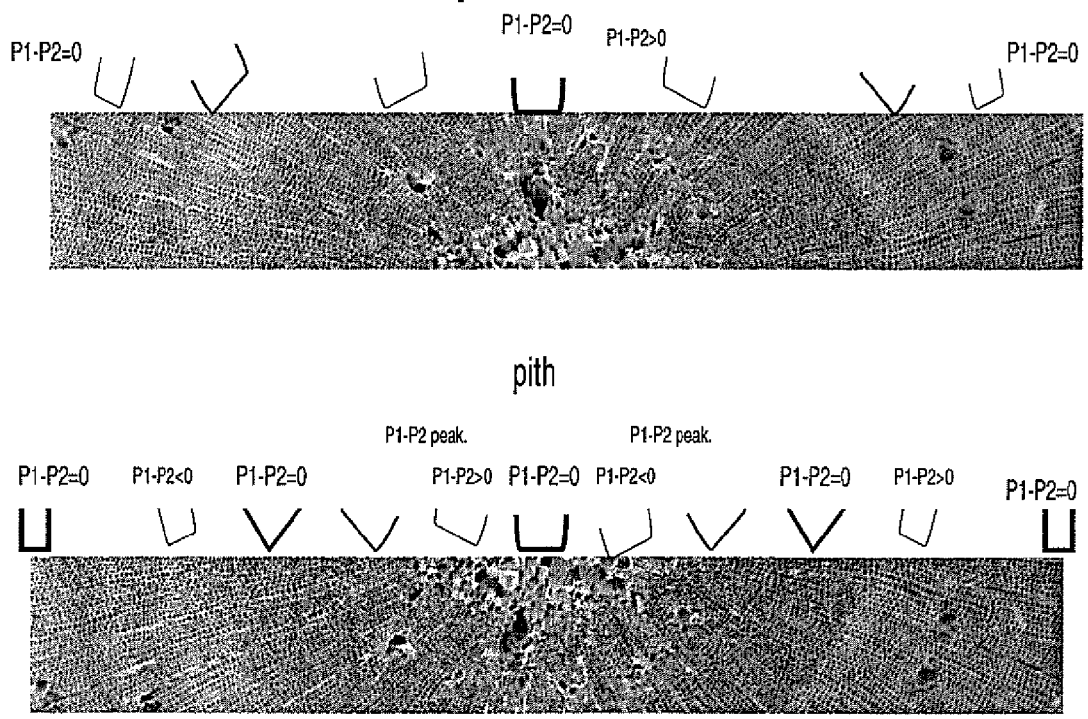
FIG. 18 is a diagram of a staple model for curvature (The staple represents the cross-section of the walls of the tracheid on the surface. A laser is at the top side of the photo, and P1 and P2 are the intensities of the sideway reflections detected at the sensor positioned at the right side and the left side of the photo, respectively.)
Figure 19:
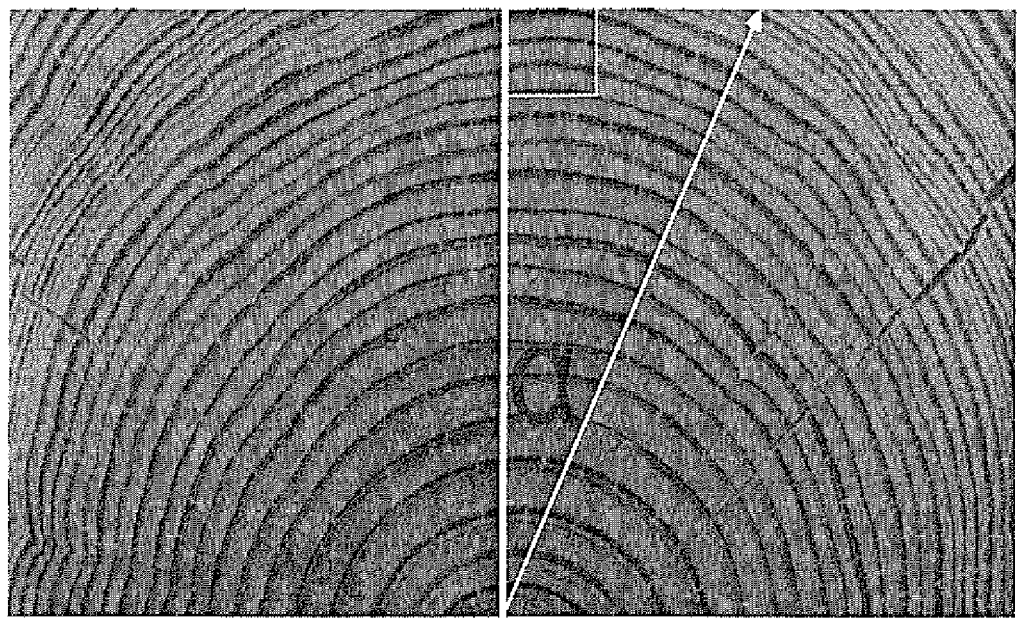
FIG. 19 is a photograph of the end of a 2 inch by 4 inch board ("2×4") showing the angle α is the direction of the file of tracheids with respect to the edge of the lumber.

Typically, the cross-section of a softwood tracheid has 4-6 corners and the same number of side walls. The overall shape of the tracheid cross-section approximates a square or a rectangle. The systematic P1–P2 patterns across a board can be explained by the "staple model", in which the staple represents the cross-section of an opened tracheid (left and right side walls bottom wall which is tangent to the ring curvature) on the surface of a piece of lumber (see FIG. 18). In the staple model, the top wall or one side wall of the rectangular has been removed. For discussion purposes, we connect a point on the surface of lumber with the pith center (FIG. 19). That line will be inclined at an angle α from perpendicular. Assuming the cross-section of the tracheid is square, then P1−P2=0 when α=0°, 45°, and 90°. Using the previously described Plessey T2 sensor composed of a ring of 72 detectors, we observed that the maximum absolute value of P1−P2 is at an angle α=22.5°, at which angle the intensity of the reflection from one side wall is minimized due to the 45° view angle.

Figure 20:
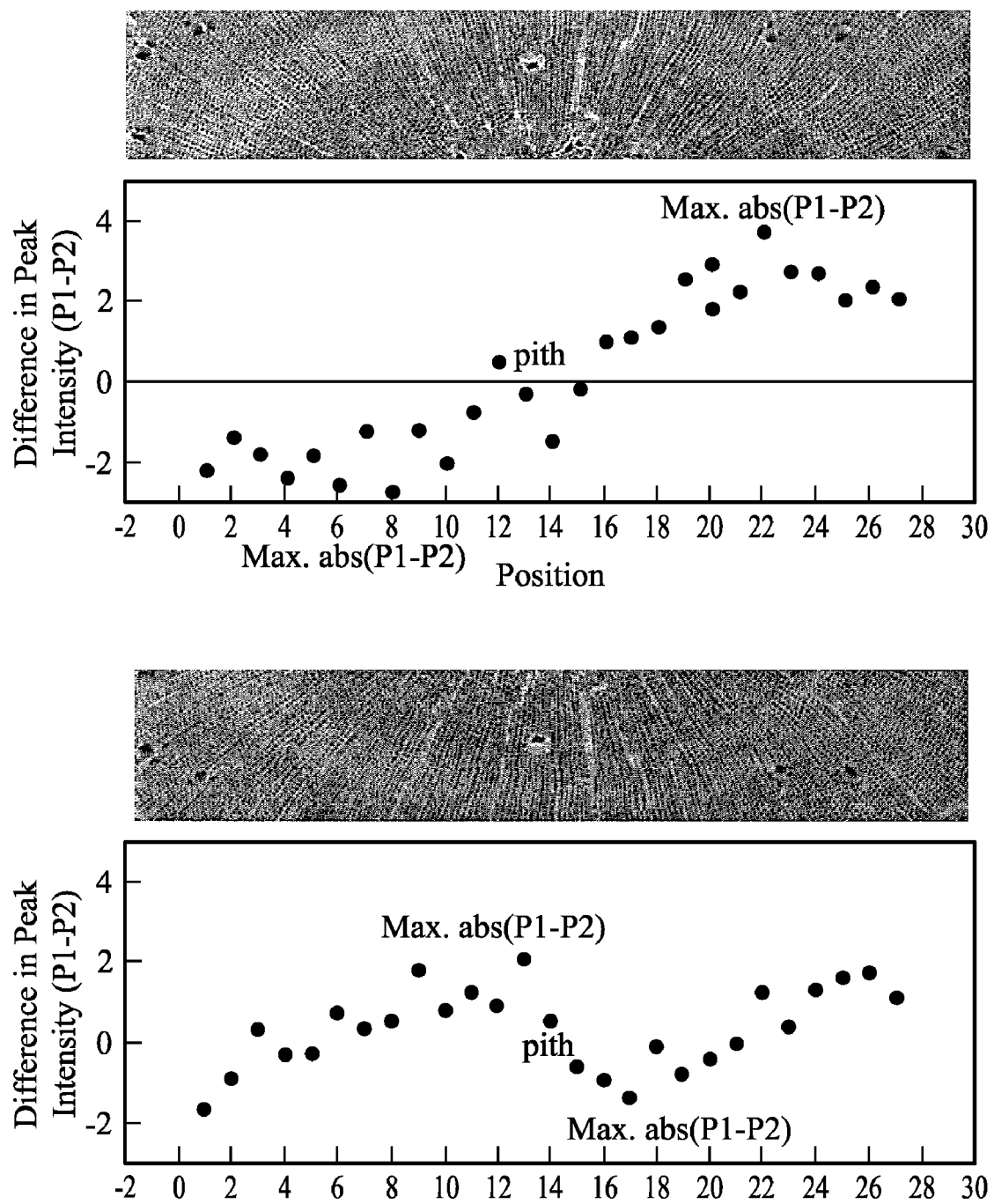
FIG. 20 illustrates P1–P2 values on the top side of a curve down (top) and up (bottom) wood sample (The x-axis is the distance in ¼" units. Note that the measurements were not taken from the SEM pictures, which were cross-sections of the stem of a loblolly pine seedling.)
Figure 21:
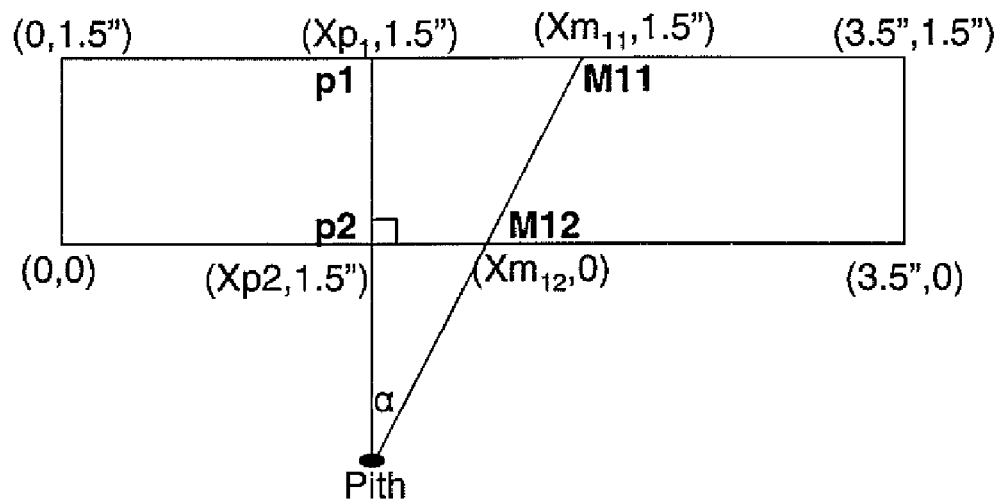
FIG. 21 is a diagram of the pith at the intersection of lines p1-p2 and M11-M12 (α=22.5° for 45° sensor angle)
Figure 22:
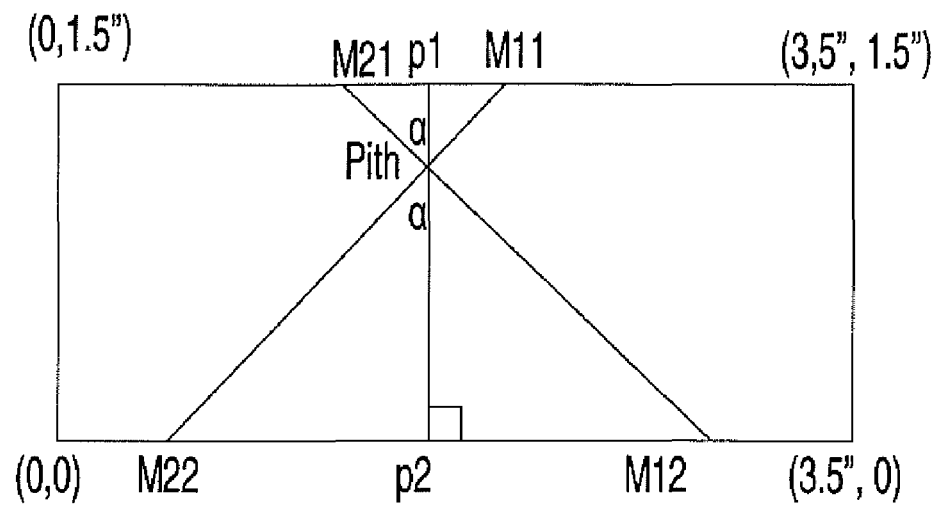
FIG. 22 is a diagram of the pith at the intersection of lines p1-p2 and M11-M22 or M21-M12 (α=22.5° for 45° sensor angle)
Figure 23:
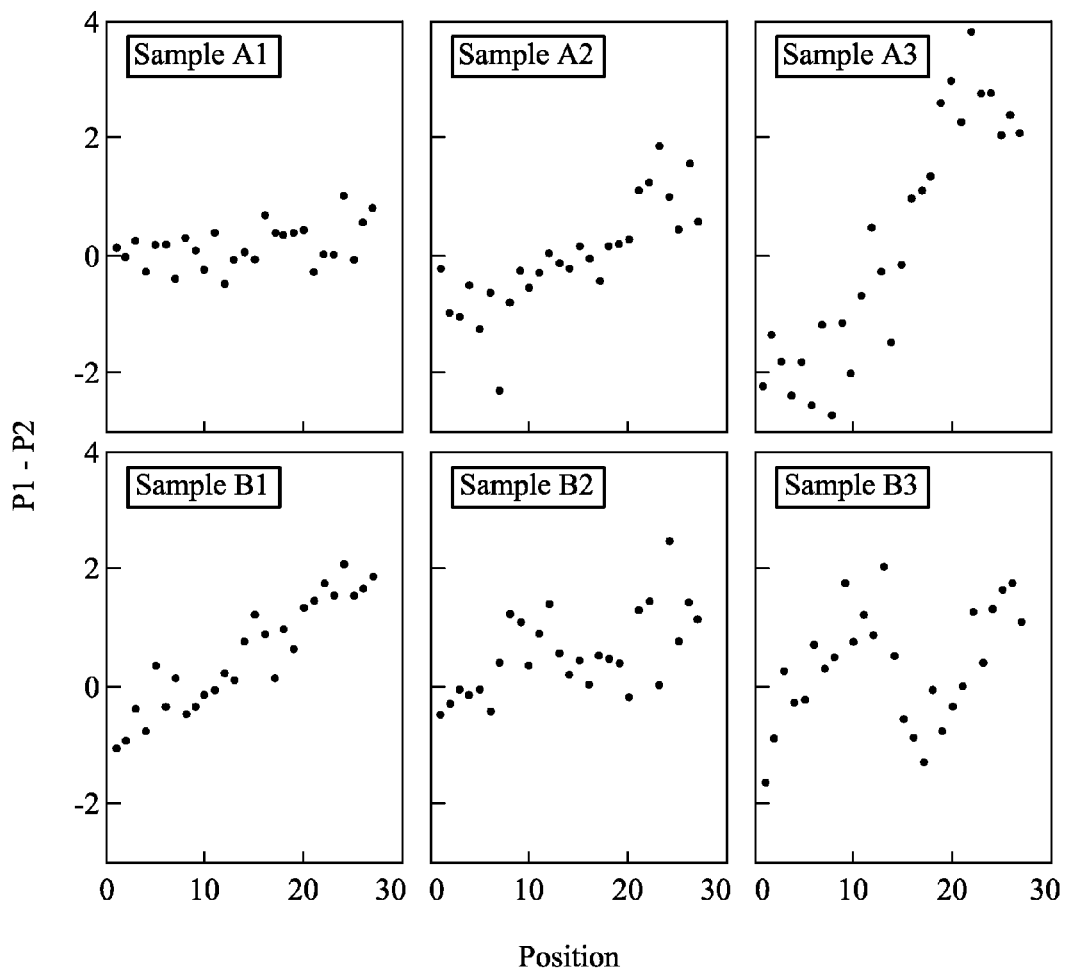
FIG. 23 illustrates plots showing the variation of P1–P2 values of Sample A (Top) & B (Bottom) in FIG. 8 (The x-axis is the distance in ¼" unit, diagrams on the left, middle and right have dive angles 15°, 7.5°, and 0°, respectively. P1–P2 was calculated by the differences of sensors around 90° and 270°, assuming zero surface angle.).

The sign and the slope of the change in the P1−P2 values near the surface location where α=0 are related to the sign and magnitude of ring curvature at that location (see FIG. 20).

If the cross-section of the tracheids is not square or the view angle is different from 45°, the value of α at these locations of maximum abs (P1−P2) will vary. This difference can be estimated mathematically or empirically. The relationship between the radius and the slope of the P1−P2 profile across the neighboring locations can be established empirically. The steeper the slope of the P1−P2 profile, the shorter the radius. The surface represented by the bottom profile in FIG. 20 is closer to the pith than the surface represented by the top profile. Consequently, the slope of P1−P2 profile near α=0 (location that is normal to the projected pith) of the top profile is gentle and that of the bottom profile is steep. Using this empirical relationship, the distance to the pith can be estimated based on the slope of the P1−P2 profile across the board.

Curve smoothing may be utilized to provide more accurate results. Normally, the orientation of the concavity on the surface of a piece of lumber is inverted on the opposite side. Therefore the sign of the slope of the P1−P2 pattern is reversed between opposite faces at their α=0 locations.

We can estimate the pith location relative to the surfaces of a lumber cross section if we can locate at least 2 points around that cross section whose vector direction to pith can be established. The pith will be located at the intersection of these two directional vectors. There are several ways of inferring these vectors. As already discussed, any points on a surface whose T2 peaks are identical (P1−P2=0) must be at an α angle of 0, 45 or 90 degrees. Similarly any surface point whose T2 peaks are maximum must be at an α angle equal to half the view angle. The needed pair of pith vectors can be derived from more than one surface. Where more than 2 pith vectors are identified, the pith location can be more accurately estimated using methods such as least squares. Another method of estimating a pith vector is to compare the P1−P2 profiles on opposite faces. Locations of equal-magnitude and opposite-sign P1−P2 profile slope indicate identical α angles. A line connecting these two opposite face points defines another pith vector.

Using one method alone may not achieve the desired accuracy in every situation, so, using complementary methods should improve the overall accuracy. Such approaches can be applied to green lumber, dry lumber, and other types of fibrous material for improving automatic grading, sorting, and other processes.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for determining properties of a wood sample, the method comprising the steps of:
    projecting a light beam at a surface of the wood sample;
    detecting intensity of reflected light at two or more locations;
    determining two local maxima of reflected light intensity; and
    determining a profile of the difference in local maxima across the surface of the wood sample;
    wherein the profile is used to determine pith location based on a pith direction, a radius of a ring curvature, and a point on the surface that is tangent to the direction of the pith.

2. The method of claim 1 wherein the point on the surface that is tangent to the direction of the pith is located by locating profile points on a plot wherein P1−P2 is equal to zero.

3. The method of claim 2 further comprising the step of:
    calculating first derivatives of the profile at each zero point on the plot.

4. The method of claim 3 further comprising the step of:
    identifying the point that is tangent to the direction of the pith as a zero cross point on the plot with a maximum derivative absolute value.

5. The method of claim 1 wherein the radius of the ring curvature is derived from an empirical relationship with a slope of the profile.

6. The method of claim 1 wherein the locations are on opposite sides of a tracheid axis for the wood sample.

7. The method of claim 6 further comprising the step of:
    calculating a surface angle for the wood sample.

8. The method of claim 7 further comprising the step of:
    using the surface angle to increase accuracy of the determined pith location.

9. The method of claim 1 further comprising the steps of:
    determining a direction vector to pith at two or more surface locations; and
    locating the pith based on the intersection of the two or more direction vectors.

10. The method of claim 9 wherein the direction vectors are obtained from multiple surfaces.

11. The method of claim 10 wherein one or more of the direction vectors is obtained by the steps of:
    locating a point on one surface;
    determining the P1−P2 profile slope at that location;
    locating a point on the opposite surface where the P1−P2 profile slope is of equal magnitude and opposite sign; and
    defining a direction vector through the two located points.

12. A method for determining properties of a wood sample, the method comprising the steps of:
    projecting a light beam at a surface of the wood sample;
    detecting intensity of reflected light at two or more locations;
    determining two local maxima of reflected light intensity; and
    determining a profile of the difference in local maxima across the surface of the wood sample;
    wherein the profile is used to determine ring curvature; and
    wherein the radius of the ring curvature is derived from an empirical relationship with a slope of the profile.

13. The method of claim 12, further comprising the step of determining a pith location based on the radius of ring curvature.

14. The method of claim 12, further comprising the steps of:
    determining a direction vector to pith at two or more surface locations; and
    locating the pith based on the intersection of the two or more direction vectors.

15. The method of claim 13 wherein the direction vectors are obtained from multiple surfaces.

16. The method of claim 14 wherein one or more of the direction vectors is obtained by the steps of:
  locating a point on one surface;
  determining the P1–P2 profile slope at that location;
  locating a point on the opposite surface where the P1–P2 profile slope is of equal magnitude and opposite sign; and
  defining a direction vector through the two located points.

* * * * *